United States Patent
Carrell et al.

(10) Patent No.: US 6,216,528 B1
(45) Date of Patent: Apr. 17, 2001

(54) METHOD AND APPARATUS FOR DETERMINING A VISCOSITY OF AN ACTUATING FLUID

(75) Inventors: Darwin R. Carrell, Edwards; Larry E. Kendrick, Peoria; Michael S. Lukich, Chillicothe; Kirk S. Shively, Dunlap, all of IL (US)

(73) Assignee: Caterpillar Inc., Peoria, IL (US)

( * ) Notice: Subject to any disclaimer, the term of this patent is extended or adjusted under 35 U.S.C. 154(b) by 0 days.

(21) Appl. No.: 09/211,626

(22) Filed: Dec. 15, 1998

(51) Int. Cl.$^7$ .................................................. G01N 11/08
(52) U.S. Cl. ...................... 73/54.01; 73/54.11; 73/54.14
(58) Field of Search ............................... 73/54.01, 54.02, 73/54.11, 54.13, 54.14

(56) References Cited

U.S. PATENT DOCUMENTS

| 5,181,494 | 1/1993 | Ausman et al. ................. 123/446 |
| 5,357,912 | 10/1994 | Barnes et al. ................... 123/357 |
| 5,423,302 | 6/1995 | Glassey ............................ 123/446 |
| 5,564,391 | 10/1996 | Barnes et al. ................... 123/446 |
| 5,634,448 | 6/1997 | Shinogle et al. . |
| 5,750,887 | 5/1998 | Schricker ......................... 73/117.3 |
| 5,896,841 * | 4/1999 | Nemoto et al. ................. 123/381 |

FOREIGN PATENT DOCUMENTS 19741164   3/1998   (DE) .................................... 123/381

\* cited by examiner

*Primary Examiner*—Daniel S. Larkin
(74) *Attorney, Agent, or Firm*—W. Bryan McPherson, III

(57) ABSTRACT

The present invention provides a method and apparatus for determining the viscosity range and/or oil grade of an actuating fluid in a fuel system. The method includes the steps of determining a flow, pressure, and temperature of the actuating fluid, and responsively determining the viscosity range and/or oil grade of the actuating fluid.

21 Claims, 6 Drawing Sheets

Fig_4_
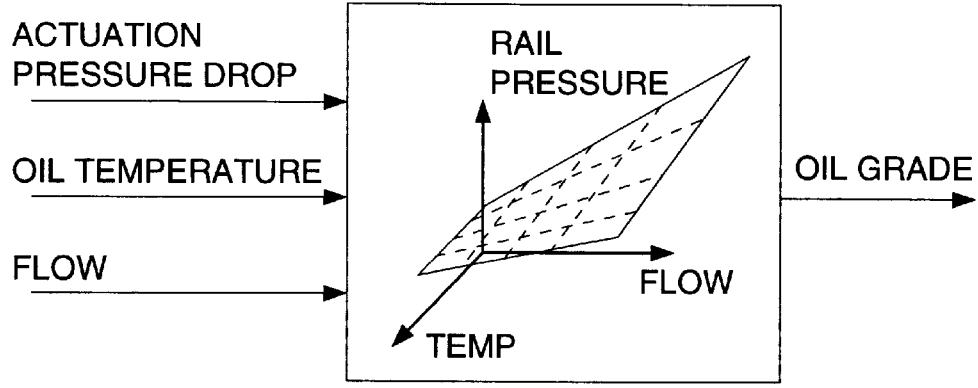
Fig_5_
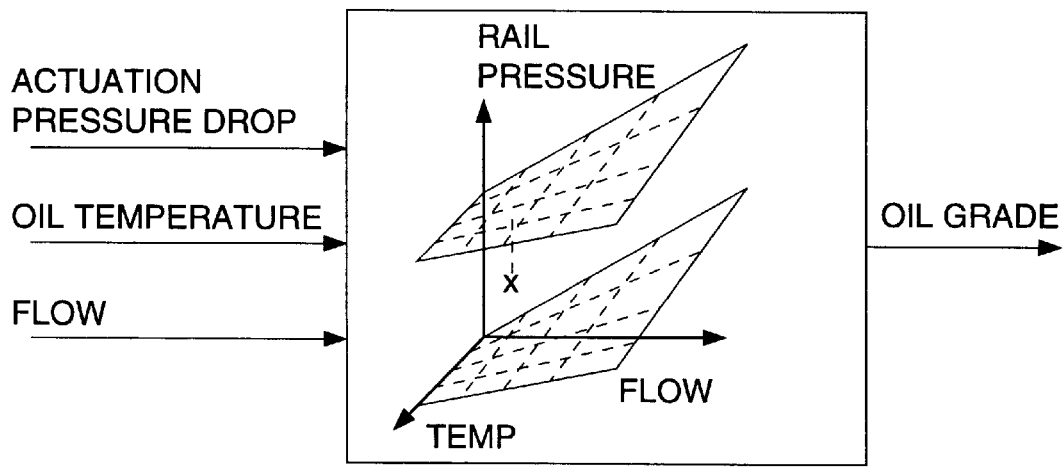

METHOD AND APPARATUS FOR DETERMINING A VISCOSITY OF AN ACTUATING FLUID

TECHNICAL FIELD

This invention relates generally to a fuel system, and more particularly, to a method and apparatus for determining a viscosity range of an actuating fluid located within a fuel system.

BACKGROUND ART

In a fuel system having hydraulically-actuated electronically controlled unit injectors (HEUI), high pressure hydraulic actuating fluid flows into a chamber, located within the injector, and pushes down on a plunger which pushes fuel out from a plunger cavity, and out the injector through a nozzle. A solenoid, located within the injector, controls when the high pressure actuating fluid is exposed to the plunger by moving a poppet valve. The amount of fuel injected is controlled by adjusting the duration the solenoid is on.

The viscosity of the actuating fluid affects both the amount of fuel delivered by the injector, and when the delivery process begins. For example, in cold temperatures the actuating fluid is thicker (more viscous) than at warm temperatures. Therefore, when an electrical signal is delivered to a solenoid, commanding the solenoid to deliver actuating fluid to the injector, the fluid flows at a slower rate into the chamber to push against the plunger. With the actuating fluid moving at a slower rate there is an increased delay before the injector begins delivering fuel. Furthermore, when the solenoid is turned off to stop delivery of the fuel, the reduced flow rate of the actuating fluid results in less total fuel being injected between when the solenoid is turned on and off. Hence, with a high viscous actuating fluid seen at cold starting temperatures as compared to higher temperature operating conditions, less fuel is delivered by the injectors and the fuel is delivered later in the crank cycle. Under these conditions, overall engine performance is adversely effected, resulting in incomplete combustion, low power, white smoke, etc.

The viscosity of the actuating fluid is a function of the fluid type, the amount the fluid is sheared from the transmission through the hydraulic circuit, and the temperature of the fluid. In an operating engine, neither the type of fluid, nor the temperature is fixed. The fuel system may use a variety of actuation fluids. For example, a more viscous SAE 15W40 engine oil or a less viscous 0W20 engine oil may be used. Also, the fuel system operates over a wide range of temperatures, e.g., −50 degrees Fahrenheit through 250 degrees Fahrenheit.

The reduction in fuel delivery and delays in fuel delivery increase as the viscosity of the actuating fluid increases. If the changes in viscosity are not accounted for, the fuel delivery and timing may be incorrect making it difficult to start and run the engine especially at high viscosities encountered at cold temperatures. If the fuel delivery is too small, the engine may not start or be underpowered. If the fuel delivery is too large, the engine structural capabilities may be exceeded, or excessive smoke may be produced. Misfire may occur due to fuel delivery at incorrect (late) ignition timings.

The present invention is directed to overcoming one or more of the problems identified above.

DISCLOSURE OF THE INVENTION

In one aspect of the present invention, a method for determining a viscosity range of an actuating fluid located within a fuel system is disclosed. The method includes the steps of determining a pressure drop and temperature of the actuating fluid, and responsively determining a viscosity range of the actuating fluid.

In yet another aspect of the present invention, a method for determining a grade of an actuating fluid located within a fuel system is disclosed. The method includes the steps of determining a pressure drop and temperature of the actuating fluid, and responsively determining the grade of the actuating fluid.

In yet another aspect of the present invention, a method for determining a viscosity range of an actuating fluid located within a fuel system is disclosed. The method includes the steps of determining a temperature and grade of the actuating fluid, and responsively determining a viscosity range of the actuating fluid.

In yet another aspect of the present invention, an apparatus for determining a viscosity range of an actuating fluid located within a fuel system is disclosed. The apparatus includes a pressure sensor adapted to sense a pressure of the actuating fluid, a temperature sensor adapted to sense a temperature of the actuating fluid, and a controller adapted to determine a viscosity of said actuating fluid in response to the pressure and temperature.

BRIEF DESCRIPTION OF THE DRAWINGS

FIG. 4 is an example of an oil grade map;

FIG. 5 is an example of multiple oil grade maps;

BEST MODE FOR CARRYING OUT THE INVENTION

Figure 1:
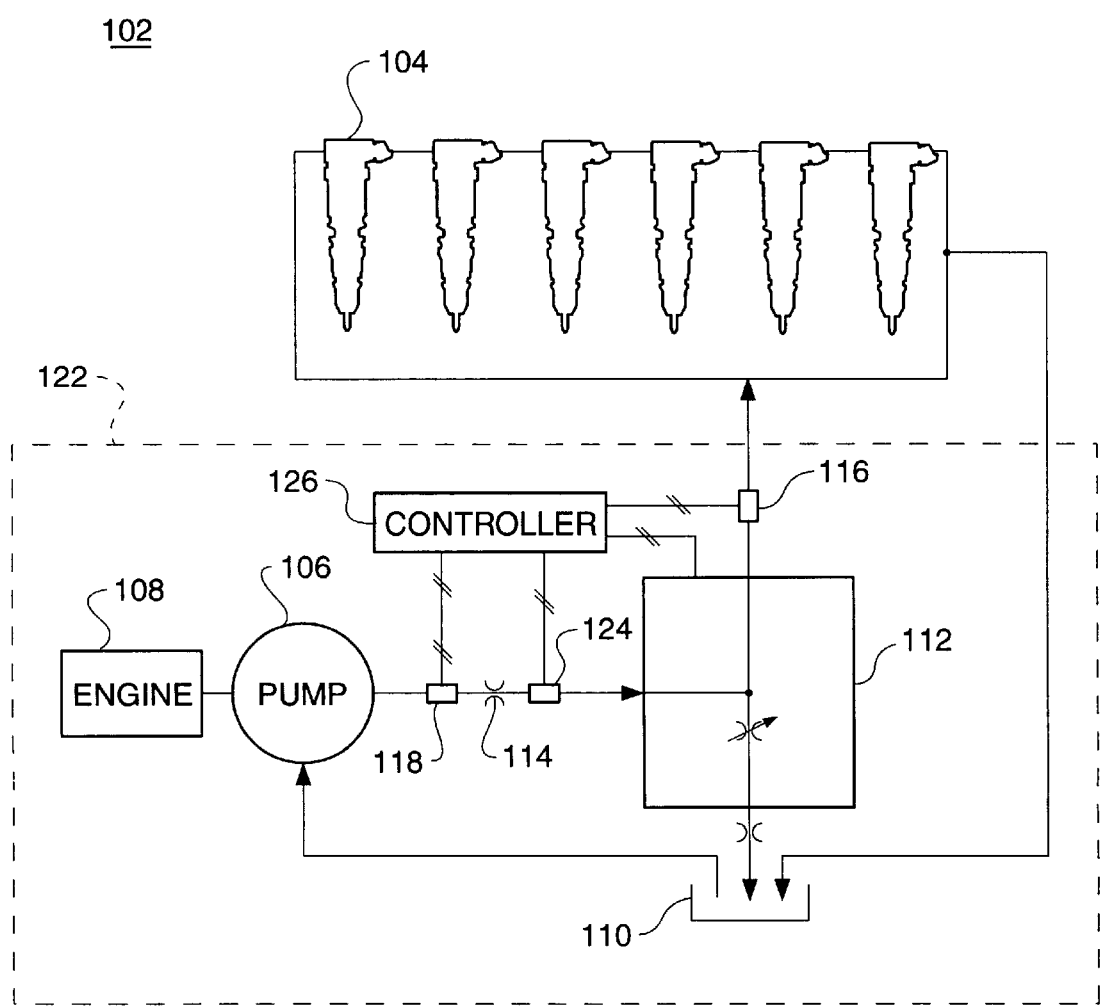
FIG. 1 is a high level diagram of one embodiment of an fuel system.

The present invention provides an apparatus and method for determining a viscosity range of actuating fluid. FIG. 1 is an illustration of one embodiment of a fuel system 102 of an engine. The fuel system 102 includes at least one hydraulically-actuated electronically-controlled injector (HEUI) 104 for each combustion chamber or cylinder (not shown) of the fuel system 102. The fuel system 102 also includes a circuit 122 for supplying actuating fluid to each injector 104. In one embodiment, the circuit 122 includes a pump 106, driven by an internal combustion engine 108. The output of the pump 106 is connected to each fuel injector 104 and also to a fluid sump (or tank) 110. The fluid sump 110 is also attached, through a return line, back to the pump 106. Each injector 104 is also connected to the fluid sump 110 in order to return the actuating fluid to the sump 110.

The circuit 122 includes a pressure sensor 116. In the preferred embodiment, the pressure sensor 116, is located between a pressure control valve 112, and the injectors 104. The pressure sensor 116 senses the pressure of the actuating fluid and responsively generates a pressure signal.

In addition, a means for determining the fluid flow is included in the circuit 122. In one embodiment, a flow sensor 118, located at the output of the pump 106, may be used to determine the flow of the fluid, and responsively generate a fluid flow signal. Alternatively, an engine speed sensor (not shown) may be used to sense the speed of the engine 108, and responsively generate a flow signal based on the sensed engine speed. In the preferred embodiment, the pump 106 is a fixed displacement pump. Therefore, the flow may be determined by multiplying the engine speed by the pump displacement per revolutions per minute of the engine speed. Alternatively, a variable displacement pump may be used if the pump is stroked to a known displacement, such as either minimum or maximum stroke, during engine cranking.

The circuit 122 includes a temperature sensor 124. The temperature sensor 124 senses the temperature of the actuating fluid, and responsively generates a fluid temperature signal. In the preferred embodiment, the actuating fluid is petroleum based oil. However, the fluid may be a synthetic oil, fuel, or other type of non-compressible fluid.

The circuit 122 includes an electronic controller 126. The controller 126 receives the pressure signal, the temperature signal, and the flow signal, and responsively determines a viscosity range of the actuating fluid.

The circuit 122 includes a pressure control valve 112 for regulating how much actuating fluid flows to the injectors 104 as opposed to the fluid sump 110. By adjusting how much of the actuating fluid flow provided by the pump 106 goes to the injectors 104 as compared to the sump 110, the pressure of the fluid supplied to the injectors 104 may be regulated. The pressure sensor 116 senses the pressure of the fluid flowing to the injectors 104 and provides feedback to an electronic controller 126. The electronic controller 126 compares a desired pressure to an actual pressure to form a closed loop system for maintaining pressure. For example, if the sensed fluid pressure exceeds the desired pressure the electronic controller 126 commands the pressure control valve 112 through an electronic signal, to increase the amount of fluid flow to the sump 110 thereby bringing the injector pressure down to the desired level.

The present invention includes a method for determining a viscosity range of an actuating fluid located within a fuel system 122. The method includes the steps of determining a flow, temperature, and pressure drop of the actuating fluid, and responsively determining a viscosity range of the actuating fluid.

Figure 2:
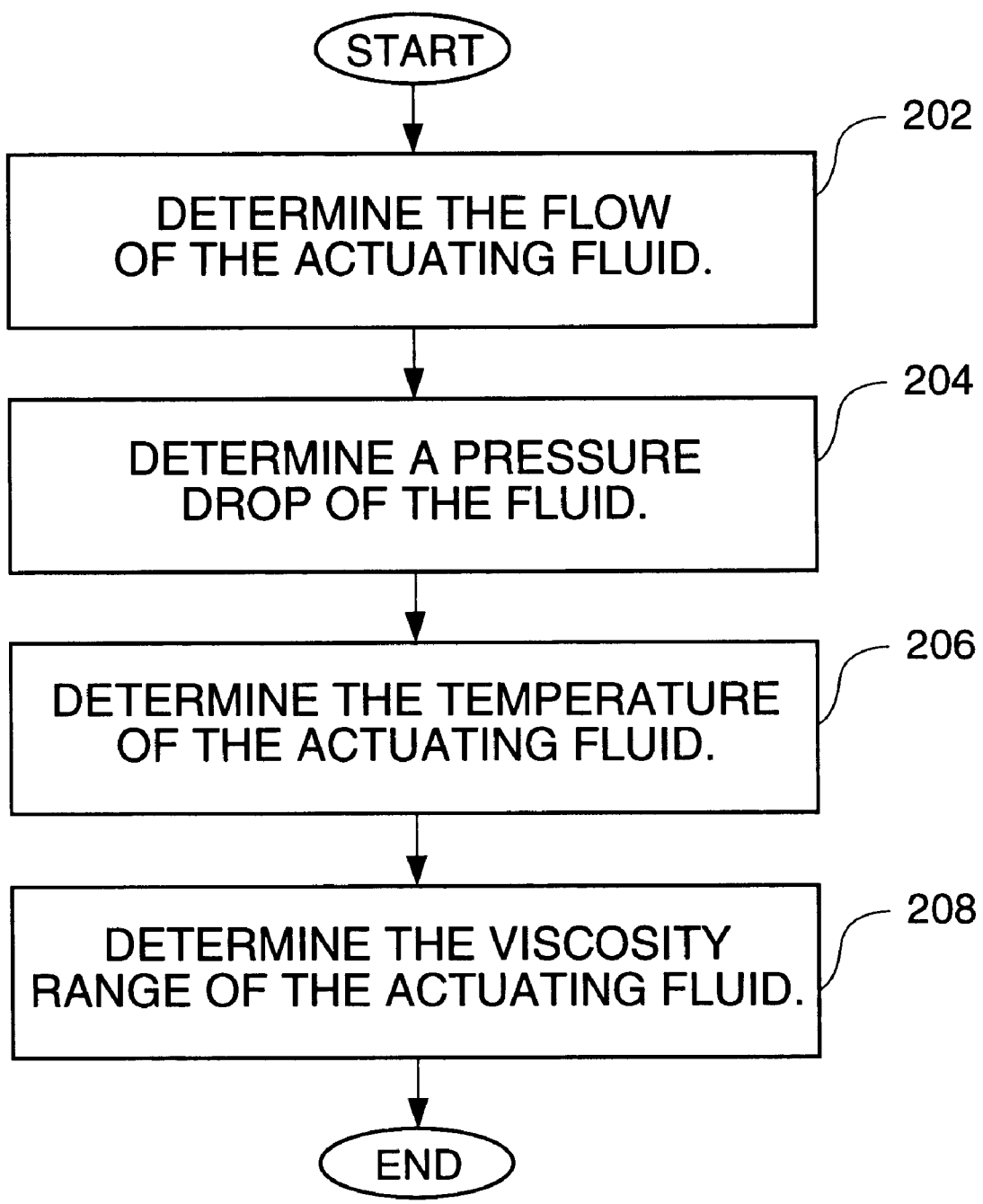
FIG. 2 is an illustration of the method for determining a viscosity range of an actuating fluid.

FIG. 2 illustrates a flow diagram of the method of the present invention. In a first control block 202, the flow of the actuating fluid is determined. As stated above, if a flow sensor 118 is not available, the fluid flow may be determined by sensing the speed of the pump 106 and multiplying the speed by the pump displacement. The speed of the pump 106 may be determined by sensing the speed of the internal combustion engine 108 driving the pump 106.

In a second control block 204, the pressure of the fluid is sensed by the pressure sensor 116, and a pressure signal is delivered to the electronic controller 126. In the preferred embodiment, the pressure is sensed in order to determine a pressure drop of the actuating fluid across a consistent orifice within the circuit 122. The term consistent in this context means that the area of the orifice is fixed for a given condition, e.g., whenever the same condition occurs, the area of the orifice will be the same. In the preferred embodiment, the pressure is determined during cranking of the engine, and the pressure drop is measured across the pressure control valve 112. During the cranking of the engine, the solenoids associated with the fuel injectors, are not activated. Therefore, the injectors 104 do not fire, and the actuating fluid does not flow through the injectors 104, albeit leakage. The fluid is circulated from the pump 106, through the pressure control valve 112, to the fluid sump 110, and back to the pump 106. During cranking, no current is provided to the pressure control valve. No attempt is made to regulate the injector pressure during cranking; therefore, the pressure control valve is used as a consistent orifice which a pressure drop may be measured across. As the fluid flows from the pump 106 through the restrictions of the pressure control valve 112 and the associated connecting lines to the sump 110, a pressure drop occurs. Therefore, all of the flow will be directed through the pressure control valve 112 to the sump 110, and the pressure drop may be measured across the pressure control valve 112. In one embodiment the pressure drop may be determined by using a pressure sensor 116 located between the injectors 106 and the pressure control valve 112. The pressure on the low side of the pressure control valve 112, i.e., at the fluid sump 110, may be assumed to be at atmospheric levels, or measured by the internal combustion engine atmospheric pressure sensor if so equipped. Therefore the output of the pressure sensor 116 may be used to sense the amount of pressure drop across the pressure control valve 112. In an alternative embodiment, another pressure sensor (not shown) may be located between the pressure control valve 112 and the sump 110. Then, the difference between the pressure reading of the pressure sensors located before and after the pressure control valve 112 will indicate the pressure drop across the pressure control valve 112.

In a third control block 206, the temperature of the fluid is sensed by the temperature sensor 124, and a temperature signal is delivered to the electronic controller 126.

In a fourth control block 208, the viscosity range of the actuating fluid is determined. One example of an actuating fluid is a petroleum based oil. In one embodiment, the viscosity range of the actuating fluid may be defined as a function of the oil grade.

Oil grade may be defined by the widely recognized SAE standard J300 "Engine oil Viscosity Classification." This specification sets the allowable viscosity for a given oil grade, as illustrated in Table 1 below.

TABLE 1

| SAE Viscosity Grade | Low Temp(C) Cranking Viscosity (cP) Max | Kinematic Viscosity (cSt) at 100C Min | Kinematic Viscosity (cSt) at 100C Max |
|---|---|---|---|
| 0W | 3250 at −30C | — | — |
| 5W | 3500 at −25C | — | — |
| 10W | 3500 at −20C | — | — |
| 15W | 3500 at −15C | — | — |
| 20W | 4500 at −10C | — | — |
| 25W | 6000 at −5C | — | — |
| 20 | — | 5.6 | 9.3 |
| 30 | — | 9.3 | 12.5 |
| 40 | — | 12.5 | 16.3 |
| 50 | — | 16.3 | 21.9 |
| 60 | — | 21.9 | 26.1 |

Two series of viscosity grades are defined, those containing the letter W and those without the letter W. Single viscosity grade oils with the letter W are defined by maximum lower temperature viscosity. Single grade oils without the letter W are based on a set of minimum and maximum kinematic viscosities at 100C. multi-viscosity grade oils ("multi-grades") are defined by both of the following criteria: maximum low temperature viscosity corresponding to one of the W grades and maximum and minimum viscosities at 100C corresponding to one of the non-W grades.

The SAE definition of multi-grade oils specifies the allowable viscosities at two temperature points. From this definition, the viscosity ranges for a given oil grade can then be interpolated for other temperatures. This interpolation depends on the relationship between viscosity and temperature for oils as defined in the empirical relationship called the MacCoull, Walther, Wright equation, illustrated below:

$$\log(\log(\text{viscosity})) = A + B \cdot \log(\text{absolute temperature})$$

where A and B are constants. The A and B values for the equation, bounding the upper viscosity range versus temperature for a given multi-grade oil, are obtained by solving the equation using the maximum viscosity points defined at both 100C and the low temperature as specified in Table 1. From this, an upper bound viscosity range for each multi-grade oil is defined per SAE J300.

Figure 3:
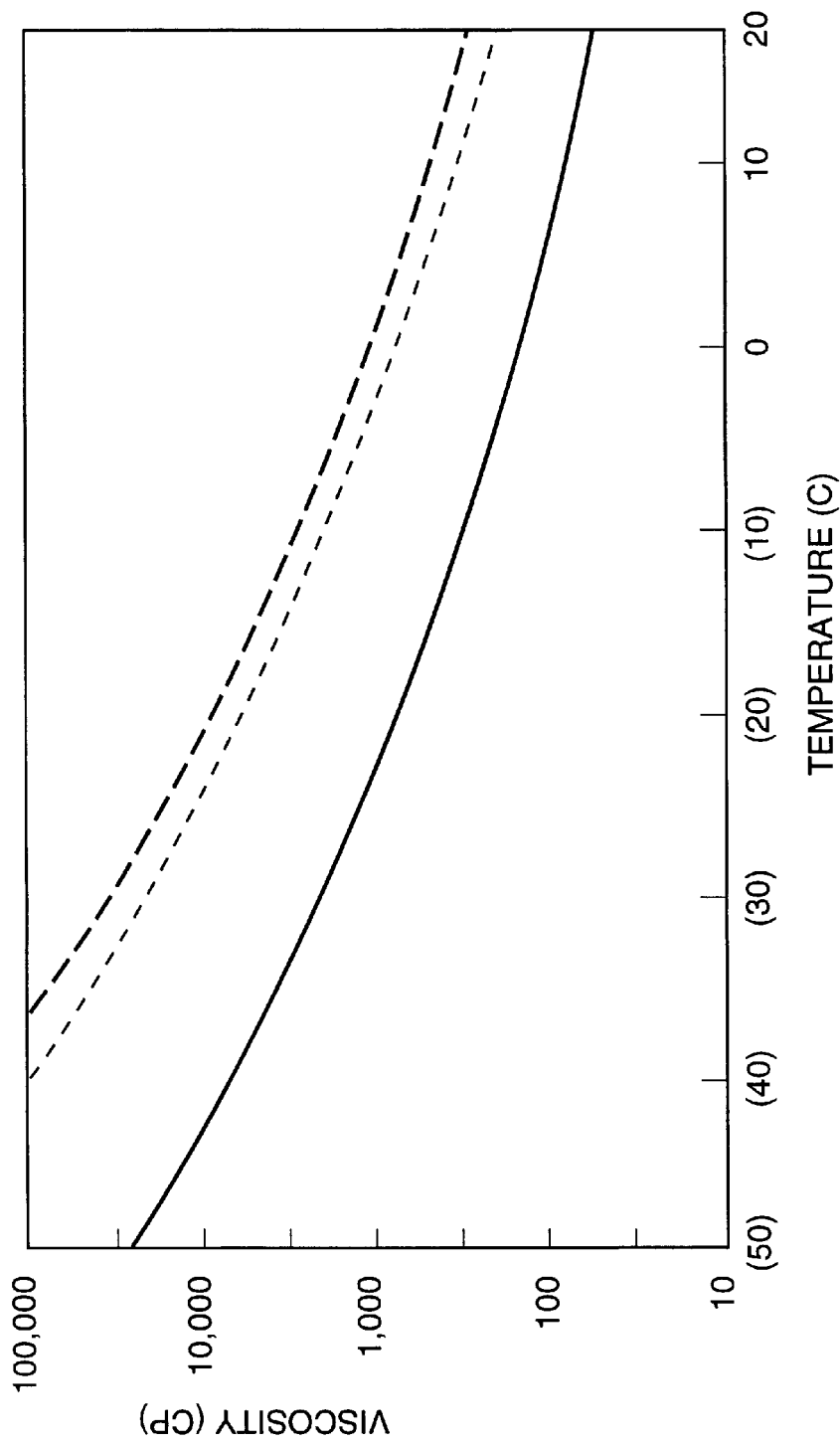
FIG. 3 is a graph of viscosity as a function of oil grade, temperature.

The viscosity of an actuating fluid, as defined in the SAE definition, is a function of the oil grade and temperature, as illustrated in FIG. 3. The oil grade, as defined per SAE J300, indicates a maximum viscosity bound of a oil for a given temperature. Therefore, once the oil grade the fluid most closely resembles, i.e., representative of the fluid, is determined, a viscosity range may be determined. The actual viscosity of the actuating fluid may be determined to be within the viscosity range. Since the oil grade defines a maximum viscosity bound, the viscosity range may be determined to be between the oil grade identified, and the next lower oil grade viscosity bound. For example, if the actuating fluid is identified to most closely resemble a 15W40 oil, and the temperature is −25C, then the viscosity range may be determined to be between 20,000 cP (15W40 @ −25C) and 10,000 cP (10W30 @ −25C). For the sake of controlling the fuel system 102, the controller 126 may either use the viscosity range, or select a viscosity within the range as the viscosity of the fluid. For the scenario described above, for example, the viscosity of the fluid may be selected to be 15,000 cP, the mid point of the identified viscosity range.

Therefore, in the preferred embodiment, the viscosity range may be determined as a function of oil grade. The oil grade which the actuating fluid most closely resembles in terms of viscosity may be determined in response to the flow, temperature, and pressure drop of the actuating fluid. A map of a particular oil grade, may be predetermined as a function of the fluid flow, pressure drop, and temperature of the fluid through empirical analysis, simulation, and testing, as illustrated in FIG. 4. For example, for a particular oil grade, the fluid temperature may be set, then the fluid flow may be varied, and the pressure drop across a consistent orifice may be measured. In the preferred embodiment, the shape of the oil grade map for a given oil grade is based on the relationship of the magnitude of a pressure drop across a consistent orifice for a given flow being directly proportional to the viscosity of the fluid.

Oil grade maps of all the potential oil grades that may be used in the fuel system may be determined in a similar manner, as illustrated in FIG. 5. During the operation of the present invention, the controller 126 receives the sensed flow, pressure drop, and temperature signals. The flow, pressure, and temperature are used to determine the oil grade most closely resembling the viscosity characteristics of the actuating fluid. The oil grade map closest to the measured parameters indicates the oil grade the actuating fluid most closely resembles. The oil grade map may be implemented as a multi-variable look up table, providing oil grade as a function of the temperature, pressure drop, and flow of the actuating fluid. Then, with the temperature and the oil grade the fluid most closely resembles, as illustrated in FIG. 3, the viscosity range may be determined as described above. Therefore, the viscosity range may be determined based on the flow, temperature, and pressure drop of the actuating fluid.

Therefore, the oil grade most closely resembling the characteristics of the actuating fluid, or the viscosity range may then be used to determine and control operational characteristics of the fuel system, including the desired fuel quantity, desired pressure of the actuating fluid, desired injection electrical duration, start of fuel delivery, and desired injection timing.

Figure 6:
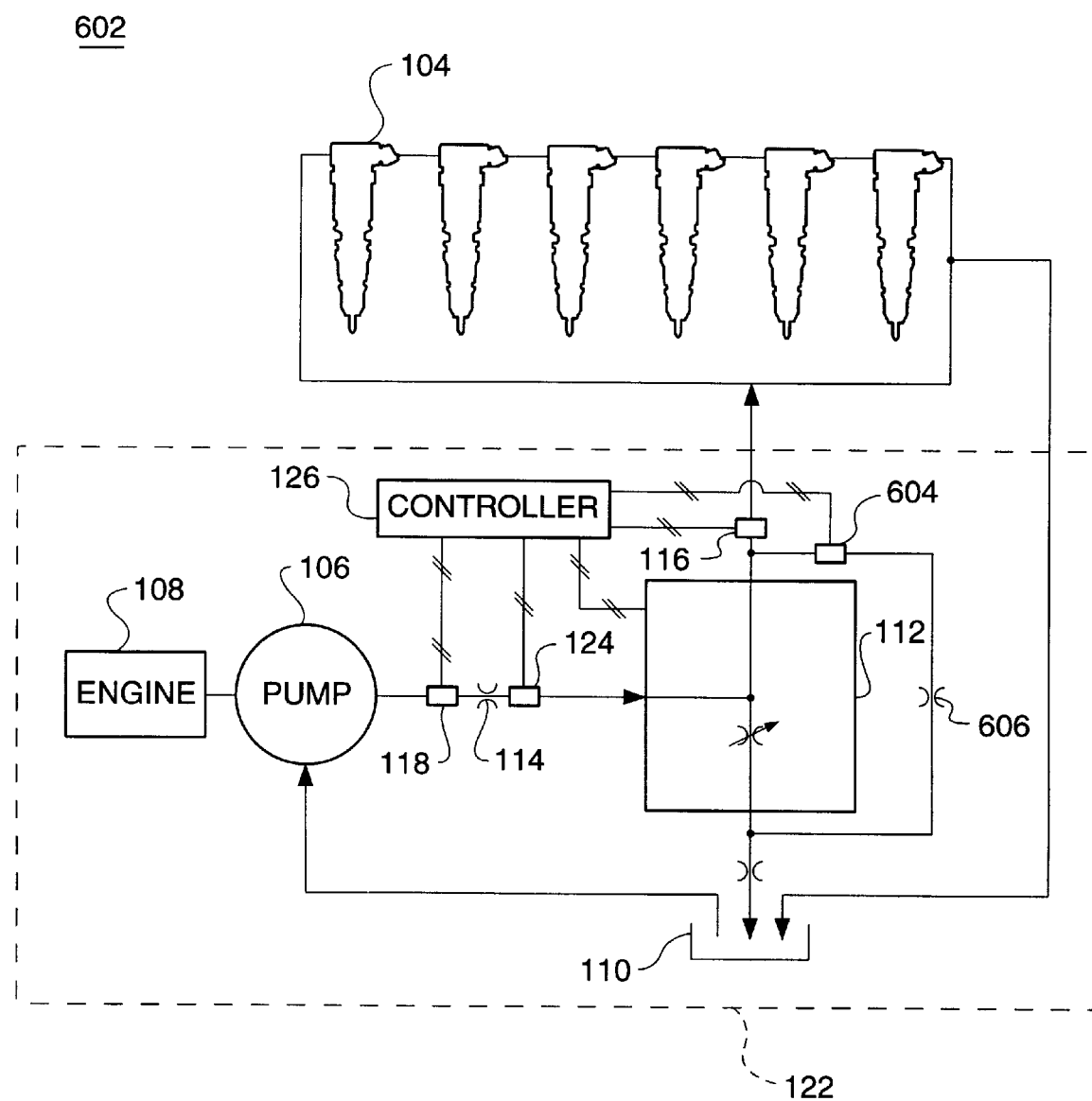
FIG. 6 is a high level diagram of an alternative embodiment of a fuel system.

As stated above, in the preferred embodiment the viscosity range is determined during cranking, in part because the pressure control valve provides a consistent orifice which a pressure drop may be measured across. In an alternative embodiment, the viscosity range may be continuously determined during the operation of the fuel system 102. FIG. 6 illustrates an alternative configuration of a fuel system 602, having a fixed geometry orifice 606 located between the fuel injectors 104 and the fluid sump 110. The fixed geometry orifice 606 provides a consistent orifice which a pressure drop may be measured across. In addition, a flow sensor 604 may be located near the consistent orifice 606 to measure the fluid flow through the orifice. Therefore, the pressure, temperature, and flow of the actuating fluid may be continuously monitored, and the oil grade and viscosity range of the fluid may be continuously determined. One advantage of this method is that, as the temperature, or other characteristics of the fluid change over the operation of the fuel system 602, the viscosity range of the fluid may be continuously updated to ensure changes in the fluid viscosity may be accounted for when determining the operational characteristics of the fuel system 602.

When the viscosity range is determined, the controller 126 may then deliver the viscosity information, such as the viscosity range, or oil grade the fluid most closely resembles, to other internal or external programs that use the information for fuel system control strategies. For example, the fuel injector on-time or a solenoid duration enables actuating fluid to flow to the injectors may be modified to ensure the proper amount of fuel is injected, and the desired injection timing is realized.

INDUSTRIAL APPLICABILITY

The present invention provides a method and apparatus for determining a viscosity range of an actuating fluid in a hydraulic-electronic fuel system. The method includes the steps of determining a flow, pressure drop, and temperature of the actuating fluid, and responsively determining the viscosity range of the actuating fluid.

Figure 7A:
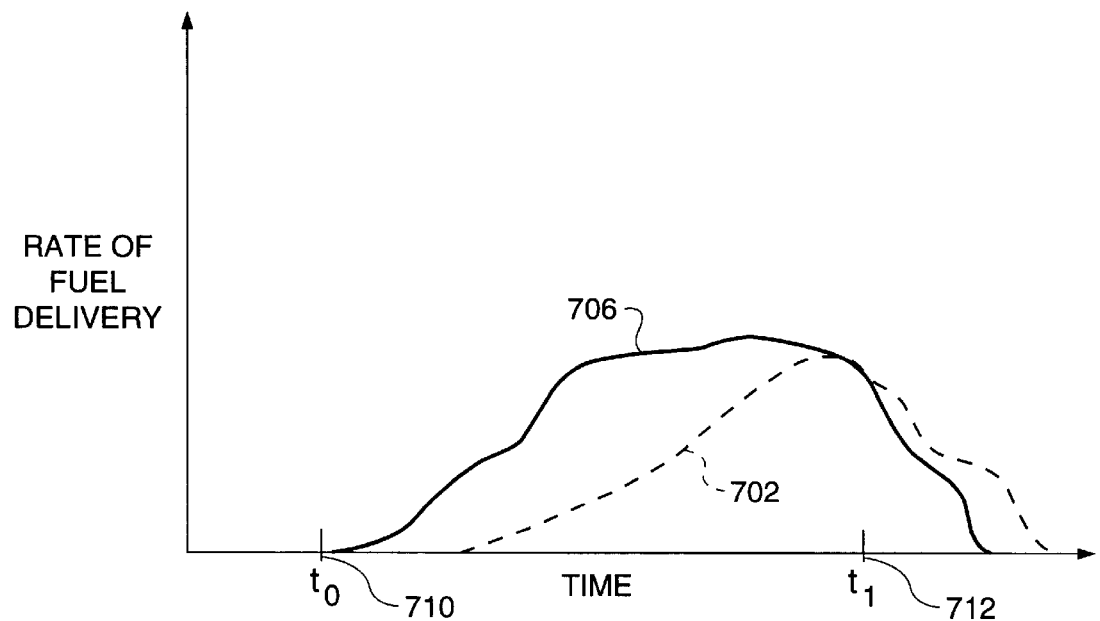
FIG. 7 is an example graph of fuel delivery as a function of time, in response to solenoid activation.
Figure 7B:
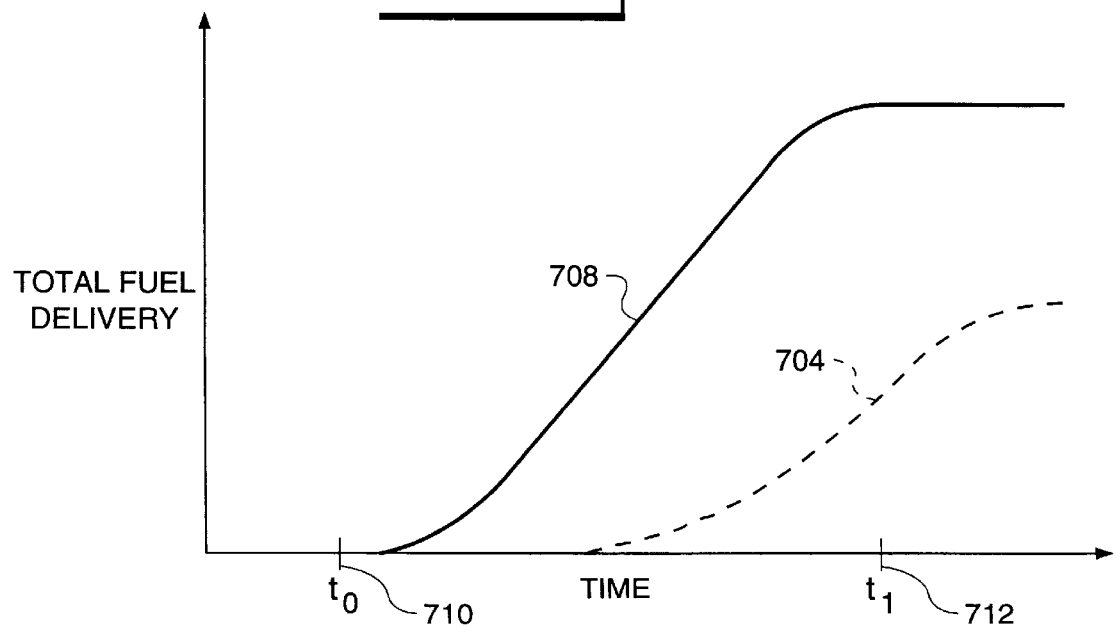

The viscosity of the actuating fluid affects both when fuel is delivered (the injection timing) and amount of fuel delivered by the injector, as illustrated in FIGS. 7A and 7B. For example, in cold temperatures the actuating fluid is thicker, i.e., has a higher viscosity (line 702, 704), than at warm temperatures (line 706, 708). Therefore, when an electrical signal is delivered to a solenoid controlling a fuel injector, commanding the solenoid to enable the delivery of actuating fluid to the injector at time $t_0$ 710, the fluid flows at a slower rate. The actuating fluid flows into a chamber within the fuel injector and pushes down on a plunger enabling fuel to pass out the injector nozzle. With the actuating fluid moving at a slower rate, there is an increased delay before the injector begins delivering fuel. Furthermore, when the solenoid is again turned off to stop delivery of the fuel at time $t_1$ 712, the reduced flow rate of the actuating fluid results in less total fuel being injected between when the solenoid is turned on and off. When an inaccurate amount of fuel is delivered by the injectors or the timing of the injection delivery shifts, overall engine performance is adversely affected.

In the preferred embodiment, during the cranking of an engine, the injectors are initially de-energized, preventing fuel from being injected. The actuating fluid is circulated from the pump 106, through a fluid pressure valve 114, a pressure control valve 112, a fluid sump 110, and back to the pump 106. The fluid flow, pressure, and temperature are sensed, and signals are respectively delivered to a controller 126. In the preferred embodiment, the actuating fluid is petroleum based oil. The controller 126 determines the viscosity range of the fluid based upon the fluid flow, temperature, and pressure drop of the fluid.

When the controller 126 determines the viscosity range of the actuating fluid, the information may be delivered to a control strategy to determine and control the operational characteristics of the fuel system including the desired fuel quantity, desired injection duration, desired injection timing, and desired fluid pressure, thereby improving the overall performance of the fuel system.

In addition, when the controller 126 determines the viscosity or grade the fluid most closely resembles, of the actuating fluid, the injectors 104 are then enabled for firing via the electrical solenoids (not shown).

In an alternative embodiment, the flow, temperature, and pressure of the actuating fluid are continuously monitored to continuously determine the viscosity range of the actuating fluid.

One of the advantages of the present invention is that as the viscosity of the fluid changes, e.g., the fluid begins to change characteristics due to use over time, the present invention will continue to dynamically determine the viscosity of the fluid and to select the grade the fluid most closely resembles. Therefore, overall system performance is not adversely effected if oil begins to break down, i.e., become less viscous over time, or the operating temperature of the engine changes.

Other aspects, objects, and advantages of the present invention can be obtained from a study of the drawings, the disclosure, and the claims.

What is claimed is:

1. A method for determining a viscosity range of an actuating fluid located within a fuel system of an engine, comprising the steps of:
   determining a flow of the actuating fluid;
   determining a pressure drop of the actuating fluid across a consistent orifice located in the fuel system;
   determining a temperature of the actuating fluid; and
   determining a viscosity range of the actuating fluid in response to said flow, and said pressure drop, and said temperature.

2. A method, as set forth in claim 1, wherein the step of determining said viscosity range further comprises the step of determining said range as a function of at least one oil grade.

3. A method, as set forth in claim 1, further comprising the steps of:
   determining an oil grade of the actuating fluid in response to said flow, pressure drop, and temperature of the fluid; and
   determining said viscosity range in response to said oil grade.

4. A method, as set forth in claim 3, further comprising the step of determining a viscosity of said fluid in response to said viscosity range.

5. A method, as set forth in claim 3, wherein the step of determining said oil grade further comprises the steps of:
   comparing said temperature, said flow, and said pressure with a plurality of oil grade maps; and
   determining said oil grade in response to said comparison.

6. A method, as set forth in claim 5, wherein the step of determining said flow further comprises the steps of:
   determining a pump engine speed;
   determining a pump displacement; and
   determining said flow in response to said pump engine speed and said pump displacement.

7. A method, as set forth in claim 1, wherein the step of determining said viscosity range further comprises the steps of:
   selecting a representative oil grade from a plurality of oil grades in response to said flow, pressure drop, and temperature of the fluid; and
   determining said viscosity range in response to said characteristic oil grade.

8. A method, as set forth in claim 1, wherein the consistent orifice is a pressure control valve.

9. A method, as set forth in claim 8, wherein the step of determining a pressure drop includes the step of determining said pressure drop of the actuating fluid across a consistent orifice of the fuel system during a cranking of the engine.

10. A method for determining a grade representative of an actuating fluid located within a fuel system of a fuel system, comprising the steps of:
    determining a flow of the actuating fluid;
    determining a pressure drop of the actuating fluid across a consistent orifice located in the fuel system;
    determining a temperature of the actuating fluid; and
    determining the grade of the actuating fluid in response to said flow, said temperature, and said pressure.

11. A method as set forth in claim 10, further comprising the step of determining viscosity range of the fluid in response to said temperature and the grade.

12. A method, as set forth in claim 11, wherein the actuating fluid is one of a synthetic oil and a petroleum based oil.

13. A method, as set forth in claim 10, wherein the step of determining the grade further comprises the step of selecting the representative oil grade from a plurality of oil grades in response to said flow, pressure drop, and temperature of the fluid.

14. A method, as set forth in claim 13, further comprising the step of determining a viscosity range in response to the representative oil grade.

15. A method, as set forth in claim 10, wherein the step of determining the grade further comprises the steps of:
    comparing said temperature, said flow, and said pressure with a plurality of oil grade maps; and,
    determining the grade in response to said comparison.

16. A method for determining a viscosity range of an actuating fluid located within a fuel system, comprising the steps of:
    determining a flow of the actuating fluid;
    determining a temperature of the actuating fluid;
    determining a pressure drop of the actuating fluid;
    determining a representative oil grade of the actuating fluid in response to said flow and said pressure; and
    determining a viscosity range of the actuating fluid in response to said oil grade and said temperature.

17. A method as set forth in claim 16, wherein the actuating fluid is an oil, said oil being one of a synthetic oil and a petroleum based oil.

18. An apparatus for determining a viscosity range of an actuating fluid located within a fuel system of an engine, comprising:

a means for determining a flow of the actuating fluid, and responsively producing a flow signal;

a pressure sensor adapted to sense a pressure of the actuating fluid across a consistent orifice located in the fuel system, and responsively produce a pressure signal;

a temperature sensor adapted to sense a pressure of the actuating fluid, and responsively produce a temperature signal; and a controller adapted to receive said flow signal, said pressure signal, and said temperature signal, and responsively determine a viscosity range of said actuating fluid.

19. An apparatus, as set forth in claim 18, wherein said viscosity range is defined as a function of at least one oil grade.

20. An apparatus, as set forth in claim 19, wherein said controller determines an oil grade representative of the fluid in response to said flow signal, said pressure signal, and said temperature signal, and determining said viscosity range in response to said oil grade.

21. An apparatus, as set forth in claim 20, wherein said controller further comprises:

one of a look-up table and a mapping means containing at least one predetermined oil grade map as a function of said flow, said pressure, and said temperature, said oil grade being determined in response to said one a look-up table and a mapping means.

* * * * *